(12) United States Patent
Watkins, Jr. et al.

(10) Patent No.: US 7,924,031 B2
(45) Date of Patent: Apr. 12, 2011

(54) HEALTH MONITORING METHOD FOR COMPOSITE MATERIALS

(76) Inventors: Kenneth S. Watkins, Jr., Dahlonega, GA (US); Shelby J. Morris, Hampton, VA (US)

(*) Notice: Subject to any disclaimer, the term of this patent is extended or adjusted under 35 U.S.C. 154(b) by 1091 days.

(21) Appl. No.: 11/510,875

(22) Filed: Aug. 23, 2006

(65) Prior Publication Data
US 2007/0166831 A1      Jul. 19, 2007

(51) Int. Cl.
*G01R 27/08*     (2006.01)
(52) U.S. Cl. ....... 324/693; 324/71.1; 324/541; 324/543; 324/544; 324/555; 324/691
(58) Field of Classification Search .................. None
See application file for complete search history.

(56) References Cited

U.S. PATENT DOCUMENTS
7,414,416 B2 *   8/2008   Watkins et al. ............... 324/693

FOREIGN PATENT DOCUMENTS
WO     WO 03/076953     9/2003

OTHER PUBLICATIONS
Sun et al., "Electrical and Mechanical Properties of Carbon Black Filled Ethylene Propylene Rubber during Thermal Oxidation Aging", Electronic Components and Technology Conference, 2003, pp. 1644-1647.*

* cited by examiner

*Primary Examiner* — Yelena G Gakh
(74) *Attorney, Agent, or Firm* — Kenneth S. Watkins, Jr.

(57) ABSTRACT

An in-situ method for monitoring the health of a composite component utilizes a condition sensor made of electrically conductive particles dispersed in a polymeric matrix. The sensor is bonded or otherwise formed on the matrix surface of the composite material. Age-related shrinkage of the sensor matrix results in a decrease in the resistivity of the condition sensor. Correlation of measured sensor resistivity with data from aged specimens allows indirect determination of mechanical damage and remaining age of the composite component.

16 Claims, 8 Drawing Sheets

HEALTH MONITORING METHOD FOR COMPOSITE MATERIALS

This application resulted, in part, from research funded by the U.S. Department of Energy. Certain rights for any intellectual property resulting from this application may apply to the Government of the United States.

This Application Claims benefit of U.S. Provisional Application No. 60/547,327 filed Feb. 24, 2004 and PCT Application No. PCT/US2005/005604 filed Feb. 23, 2005.

FIELD OF THE INVENTION

The present invention relates to health monitoring of composite materials, and, more particularly, to health monitoring of polymeric composite materials by use of conductive composite age sensors.

BACKGROUND OF THE INVENTION

Polymeric materials degrade with age, especially in severe environmental conditions. Degradation may be (1) chemical, such as chain scission and cross-linking, (2) physical, such as loss of volatile fractions and environmentally induced macroscopic changes such as crystallinity, and physical changes due to a tendency for thermodynamic equilibrium, and (3) mechanical damage such as cracking and delamination. Due to the increasing use of polymers in consumer products, transportation industries, military applications and commercial and industrial processes, there is a growing need for monitoring of the condition and remaining age of these materials before unsafe conditions or degraded performance occurs.

Composite materials find use where mechanical properties such as strength and rigidity are important. Non-destructive health monitoring of composite materials includes visual inspections, radiography, and acoustic methods. While these methods are effective for some applications, they suffer several serious disadvantages. For example, visual inspections are useful only on components with full visual access, and are not effective for flaws below the surface of the component. Radiography requires access to the components and it is time consuming and requires special training for evaluation of the results. The equipment is very expensive and subject to considerable controls to prevent radiation damage to personnel and equipment. Acoustic methods such as ultrasonic inspections require specialized equipment, considerable operator training, and good access to the component. All of these methods are effective only in detecting actual mechanical flaws such as cracks, and are not effective in predicting deterioration of the composite prior to development of the mechanical flaws.

An improved method is needed to monitor the health of composite materials which overcomes the drawbacks of current methods.

OBJECTS AND SUMMARY OF THE INVENTION

Therefore, an object of the present invention is to provide a sensor and method for monitoring the condition of composite materials.

Another object is to provide a health monitoring method for composites which provides indication of deterioration of the composite before mechanical degradation such as cracks or delamination occurs.

Another object is to provide a health monitoring method for composites which is capable of detecting chemical and physical aging early in life.

Another object is to provide a health monitoring method for composites which detects mechanical damage.

Another object is to provide a health monitoring method for composites which does not require visual or physical access to the component being monitored.

Another object is to provide a health monitoring method for composites which utilizes simple, inexpensive equipment.

Another object is to provide a health monitoring method for composites which does not require extensive training for field use.

Another object is to provide a health monitoring method for composites which does not require visual or physical access to the component being monitored.

Still another object is to provide a health monitoring method for composites which is compatible with wireless monitoring.

The method of the present invention determines the condition of a composite component by measurement of the resistivity of a conductive composite sensor formed from a polymeric matrix and conductive particles and comparing the resistivity of the sensor with the resistivity of aged sensors and component specimens to (1) correlate indirectly the resistivity measurement with mechanical properties of the component and (2) determine the remaining life of the component. The resistance of the sensor may be easily measured in the field over the life of the component. The calculated resistivity of sensor is compared to the resistivity of aged specimens to correlated condition of the sensor and, indirectly the component. The aged specimens may be naturally or acceleration aged and resistivity and mechanical properties measured for correlation with sensor data.

The polymeric matrix of a composite component ages by chemical and physical aging and by mechanical damage. Chemical aging affects the polymeric chains, for example by chain scission and crosslinking. Physical aging changes the macroscopic nature of the polymeric structure such as packing density (crystallinity or the tendency to reach the lowest energy level) of the structure, and physical changes such as loss of volatile fractions at elevated temperatures. Mechanical damage is the occurrence of mechanical defects such as cracks or delamination of the composite structure, for example from cyclic mechanical or thermal stresses. These mechanical defects become more likely after chemical aging effects that result in reduced elongation at break (EAB) of the matrix.

Several chemical and physical aging mechanisms such as chain scission, cross-linking and loss of volatiles result in volumetric shrinkage of the polymeric matrix. A conductive composite sensor, incorporating conductive particles will show a decrease in resistivity due to the shrinkage of the matrix as shown in U.S. Utility application Ser. No. 10/506,518, hereby incorporated as reference.

In the preferred embodiments, the matrix of the sensor utilizes the same or similar polymer as the composite component. The sensor may be bonded to a surface of the composite component, or it may be integrated as a region such as a strip interior to the component. In other embodiments, a "standard" sensor capable of indicating integrated time-temperature aged conditions by measurement of resistivity is used as a "standard" age-measurement device. The integrated time-temperature age condition is measured against aged composite component specimens to indirectly correlate mechanical properties and remaining age of the component.

The resistance of the sensor may be measured by a simple resistance-measuring device such a high range ohmmeter. The resistance may be measure by direct contact with the sensor, or it may be read by electrodes bonded or embedded in the sensor. Wired or wireless methods may be used to communicate resistance readings to other equipment for storage and processing.

In still another embodiment, the composite component is made into a sensor itself by addition of conductive particles to the component matrix and the resistivity of the component itself is monitored. Condition of the component may be determined by measurement of the resistivity of the component and correlated with aged specimens of the component material. Electrode pairs, either bonded to the component, or manually or automatically located provides resistance measurements for analysis. Initial measurements of the component measured at several locations and through several axes of the component provide a baseline measurement for comparison with later measurements.

In the preferred embodiments, conductive particles are selected to be chemically inert for the matrix under the expected environmental conditions of the component. Carbon particles such as those in the form of carbon black provide a low-cost conductive filler for many applications. In other applications, other carbon forms such as carbon nanotubes provide advantages such as lower volume requirements for the desired initial resistivity, and strength improvements in a composite. In still other applications, metallic particles such as silver, aluminum, nickel and copper may be used. Metallic oxides and semi-conductor materials may also be used.

In the preferred embodiments, the conductive filler is adjusted to obtain the desired initial resistivity without unacceptable degradation of mechanical properties. The resistivity range between the intrinsic resistivity of the matrix and conductive particles may be enormous, in some cases more than 16 decades. The greatest sensitivity for detecting age-related shrinkage of the polymeric matrix is in the steepest portion of the resistivity-volume fraction curve of the conductive composite. Typically this occurs over several decades approximately in the midpoint of the log-resistivity vs. volume fraction curve of the sensor composite curve. Sensitivity is typically low within one or two decades of either the intrinsic resistivity of the matrix and the conductive particles. In the preferred embodiments of all the sensors disclosed in this specification, the initial resistivity is adjusted by addition of conductive particles to be in a range between two decades below the intrinsic resistivity of the sensor matrix and two decades greater than the intrinsic resistivity of the conductive particles. In the more preferred embodiments, the initial resistivity is adjusted to be in a range between three decades below the intrinsic resistivity of the sensor matrix and three decades greater than the intrinsic resistivity of the conductive particles. In the still more preferred embodiments, the initial resistivity is adjusted to be in a range between four decades below the intrinsic resistivity of the sensor matrix and four decades greater than the intrinsic resistivity of the conductive particles. In the most preferred embodiments, the initial resistivity is adjusted to be in a range between five decades below the intrinsic resistivity of the sensor matrix and five decades greater than the intrinsic resistivity of the conductive particles.

In the preferred embodiments, the initial resistivity is selected to be within five decades of the steepest portion (most sensitive) of the log-resistivity vs. volume fraction curve of the selected sensor composite. In the more preferred embodiments, the initial resistivity is selected to be within four decades of the steepest portion (most sensitive) of the log-resistivity vs. volume fraction curve of the selected sensor composite. In the still more preferred embodiments, the initial resistivity is selected to be within three decades of the steepest portion (most sensitive) of the log-resistivity vs. volume fraction curve of the selected sensor composite. In the still more preferred embodiments, the initial resistivity is selected to be within two decades of the steepest portion (most sensitive) of the log-resistivity vs. volume fraction curve of the selected sensor composite. In the most preferred embodiments, the initial resistivity is selected to be within one decade of the steepest portion (most sensitive) of the log-resistivity vs. volume fraction curve of the selected sensor composite.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

The following is a description of the preferred embodiments of a condition sensor for composite materials and a method for determining the condition of the composite material by measurement of the resistance of the condition sensor.

Figures 1, 1A:
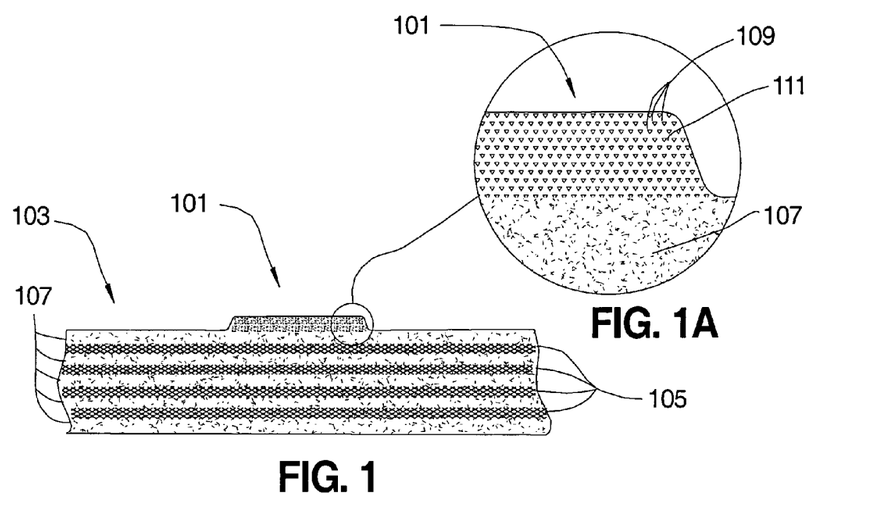
FIG. 1 is a cross section drawing of a conductive composite condition sensor disposed on the surface of a composite material.
FIG. 1A is a detail cross section drawing of the condition sensor of FIG. 1 bonded to the matrix portion of a composite component.

FIG. 1 is a cross section drawing of a preferred embodiment of a conductive composite condition sensor 101 for a composite material 103. Composite material 103 is made of a reinforcement fiber such as reinforcement fabric 105 dispersed in a thermoplastic or thermoset polymer matrix 107. Reinforcement fabrics include fibers made of metallic, carbon, glass, boron, ceramic and polymeric fibers. The reinforcement fibers may be in woven or non-woven mats, or they may be dispersed in the matrix. Matrix material 107 includes thermoplastic materials such as polyamides, polyolefins and fluoropolymers, and thermosets such as epoxies and polyesters.

As shown best in FIG. 1A, condition sensor 101 consists of conductive particles 109 such as carbon black particles dispersed in a polymeric sensor matrix 111. The addition of conductive particles 109 to sensor matrix 111 results in a conductive composite having an electrical resistivity vs. conductive particle volume fraction response similar to that shown in the curve of FIG. 2.

Condition sensor 101 provides an indirect measurement of composite material 103 condition including degradation due to chemical aging, physical aging, and mechanical damage. Chemical aging results in volumetric shrinkage and densification of the polymer matrix due chemical aging mechanisms such as chain cross-linking and chain scission. Physical aging includes loss of matrix volatile components, resulting in an increase in volume fraction of the conductive particles 109. Physical aging also results in a reduction of free-volume of polymeric material below the glass transition temperature with time. Mechanical damage includes cracking such as micro cracks, and delamination. Mechanical damage may be caused by mechanical stresses such as thermally-induced stress and cyclic stresses such as fatigue and vibration.

Both chemical and physical aging result in an increase volume fraction of the conductive particles as compared to the matrix portion as the matrix ages, assuming the conductive particles are selected to be inert in the environmental conditions present in the composite. Therefore, resistivity R tends to decrease as the matrix material ages in a direction 202 along curve 201 during the aging process. This is because the volume of the matrix decreases with age while the volume of the conductive filler particles remains constant. The change in the volume fraction, as shown in the percolation curve of FIG. 2 results in a decrease of resistivity as the volume fraction of the conductive particles increases.

Figure 2:
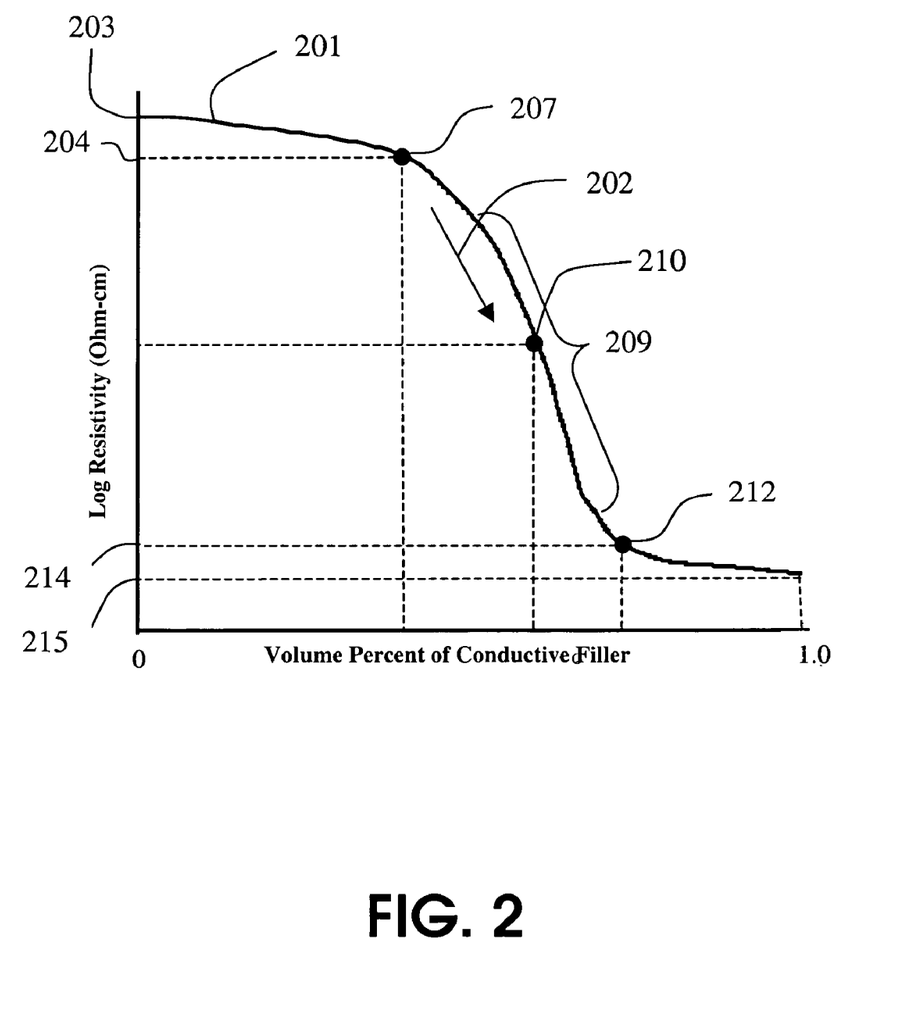
FIG. 2 is a log-resistivity vs. volume percent conductive filler curve for a typical conductive composite condition sensor.

In the preferred embodiments, a sufficient quantity of conductive particles 109 are added to matrix 111 to adjust the electrical resistivity of conduction sensor 101 in a sensitive range 209 of the electrical percolation curve shown in FIG. 2.

FIG. 2 is an electrical percolation curve 201 showing the log of the electrical volume resistivity R as a function of volume fraction $V_{FC}$ of the conductive particles:

$$V_{FC}=V_c/V_T=V_c/(V_c+V_M)$$

Where $V_c$ is the volume of the conductive particles, $V_M$ is the volume of the matrix and $V_T$ is the total volume of the conductive particles and the matrix.

The resistivity 203 at $V_{FC}=0$ represents the inherent resistivity of the matrix (no conductive particles, $V_{FC}=0$) and is typically in the region of insulators for many unfilled polymers ($R=10^{10}$ to $10^{18}$ ohm-cm.). As the volume fraction of conductive particles $V_{FC}$ is increased, there is very little reduction in resistivity since no significant conduction paths are established in the composite. As $V_{FC}$ is further increased until the lower percolation threshold (region of point 207) is reached a sufficient quantity of conductive paths of the conductive filler is established to so that the volume resistivity R begins to decrease significantly as demonstrated by the deflection in curve 201 at point 207.

Further increases in $V_{FC}$ result in a rapid decrease of resistivity as the volume fraction of the conductive particles is increased by a small amount. This region of high sensitivity to $V_{FC}$, shown in region 209 of curve 201, includes the steepest (inflection) portion 210 of curve 201 and includes portions of the curve above and below deflection point 210 where the steepness of curve 201 is less than the inflection point, but greater than the threshold values. Further increases in $V_{FC}$ produce the upper percolation threshold (region of point 212) where there exist substantial conductive paths as a result of the conductive filler so that further increases in $V_{FC}$ produce only small changes in the resistivity of the composite. At $V_{FC}=1$, no matrix is present, and the value of R approaches the intrinsic value 215 of the conductive particles, typically less than 1 ohm-cm and more commonly $1.5\times10^{-6}$ to $10^{-2}$ ohm-cm for metallic, metal oxide and semi-metallic fillers.

In practice, the upper 212 and lower 207 percolation thresholds are not distinct points observable on the resistivity vs. $V_{FC}$ curve. For the use of this disclosure, the lower percolation threshold for $V_{FC}$ (point 207) is the value corresponding to a resistivity (point 204 of FIG. 2) one order of magnitude less than the resistivity of the matrix alone. The resistivity of the matrix portion is the value at $V_{FC}=0$, corresponding to point 203 of FIG. 2. Likewise, the upper percolation value for $V_{FC}$ (point 212) is the value corresponding to a resistivity (value 214 of FIG. 2) one order of magnitude greater than the inherent resistivity of the conductive particles. The resistivity of the conductive particles is the value at $V_{FC}=1$, corresponding to point 215 of FIG. 2.

Typical conductive fillers are carbon black, carbon nanotubes and metallic particles such as silver, nickel and aluminum, although other conductive and semi-conductive particles such as metallic oxides can be used. In the preferred embodiments, the conductive particles are highly structured particles such as highly structured carbon black particles or nanotubes to reduce the volume fraction of conductive particles required. In other embodiments, less-structured particles are used to increase the steepness of curve portion 209.

The values of resistivity R at the lower percolation threshold 207, inflection point 210 and upper percolation threshold 212 will vary with the composite. The percolation thresholds may be associated with a sharp departure from the intrinsic resistivity of the matrix and filler, or it may be a gradual departure.

In the preferred embodiments, sensor matrix 111 is a high-resistivity (insulative) thermoplastic or thermoset polymer. In the most preferred embodiments, sensor matrix 111 is the same matrix as used in composite matrix 107.

In the preferred embodiments, the type of conductive particles and volume fraction of the conductive particles $V_{FC}$ are selected to provide the desired level of sensitivity of condition sensor 101 and provide a range of resistivity that can be measured by the selected instrumentation. The sensitivity of the sensor is determined by the steepness or slope of curve 201, the most sensitive portion being the portion of the curve 209 including, and adjacent to, the point of steepest slope (210). The value of resistivity is chosen so that the desired dimensions of the sensor and resistivity provide a range of resistance that can be read by the selected resistance-measuring instrument.

For example, the resistivity R of lower percolation value 204 is not in a high sensitive measurement portion of the curve since the slope of curve is low at point 207. Also, since resistivity at point 204 is typically one order of magnitude less than the resistivity of the matrix, an insulator, sensors of a practical size would result in sensor resistances far higher than field instrumentation would allow. On the other hand, the upper percolation value 214 would also provide poor sensitivity since the slope of curve 201 is low in this region.

Ideally, the filler type and content is adjusted so that $V_{FC}$ is approximately at the steepest point 210 of curve 201 at the beginning of aging. In this manner, sensitivity of the decrease in volume fraction $V_{FC}$ due to aging and measured by the resistance of the sensor is greatest at the beginning of life. A higher value of $V_{FC}$ may be chosen for practical reasons, for example to make electrical measurement of the sensor resistance easier at the expense of some sensitivity of the measurement. In the preferred embodiments, a practical target sensor utilizes a filler type and quantity for the starting resistivity R to be from one-tenth to nine tenths (on a log scale) of the total range of resistivity from the intrinsic resistivity of the filler to the intrinsic resistivity of the matrix. In the more preferred embodiments, the sensor utilizes a filler type and quantity for the starting resistivity R to be from one-fourth to three fourths (on a log scale) of the total range of resistivity from the intrinsic resistivity of the filler to the intrinsic resistivity of the matrix. In the still more preferred embodiments, the sensor utilizes a filler type and quantity for the starting resistivity R to be from one-third to two thirds (on a log scale) of the total range of resistivity from the intrinsic resistivity of the filler to the intrinsic resistivity of the matrix. In the most preferred embodiments, the sensor utilizes a filler type and quantity for the starting resistivity R to be from two fifths to three fifths (on a log scale) of the total range of resistivity from the intrinsic resistivity of the filler to the intrinsic resistivity of the matrix.

As a polymer ages, $V_{FC}$ increases as the polymeric fraction densities due to crosslinking, chain scission, and loss of volatile fractions. Due to the steepness of the percolation curve, a small increase of $V_{FC}$ due to aging is sensed by a decrease in resistivity R. Data such as resistivity and mechanical property measurements from accelerated aging, such as that disclosed in PCT application 60/362,157 (currently PCT/US03/06844, hereby incorporated by reference) provides data for empirical correlation of material properties by measurement of sensor resistivity.

Example

Figure 3:
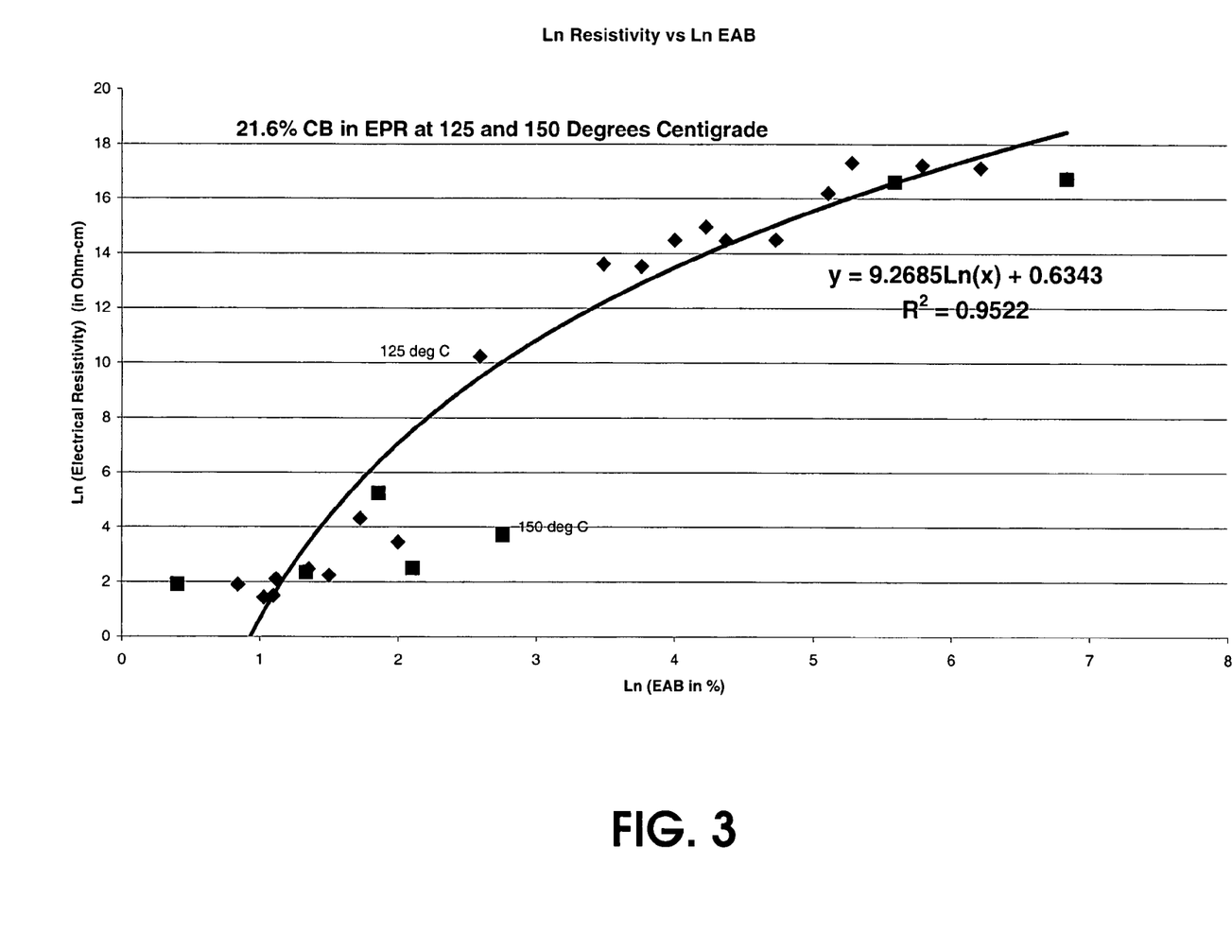
FIG. 3 is a Ln resistivity vs. Ln elongation-at-break curve for ethylene propylene rubber taken at two temperatures, showing correlation of resistivity of a sensor and mechanical properties.

FIG. 3 is a chart showing correlation of elongation-at-break (EAB) as a function of resistivity for ethylene propylene rubber (EPR) composite samples. The conductive filler is carbon black and the loading is 26.5% by weight. The resistivity and EAB data was collected from EPR composite samples oven aged at 125 C and 150 C and data plotted on log scales. Mechanical properties such as EAB of the base polymer (without fillers) may be measured and correlated with the composite sample.

Figures 4, 5, 5A:
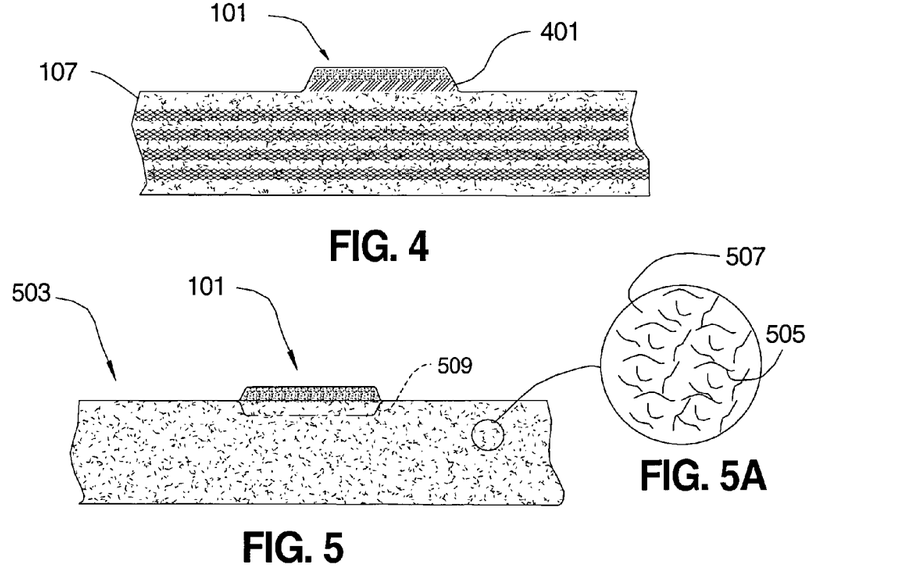
FIG. 4 is a cross section of a condition sensor bonded to a composite component utilizing a bonding/interface layer between the condition sensor and the matrix of the composite component.
FIG. 5 is a cross section of a condition sensor bonded to a composite material which utilizes strength fibers dispersed in the composite matrix.
FIG. 5A is a detail cross section of the composite material of FIG. 5.

FIG. 4 is an alternative embodiment of the invention showing bonding or interface layer 401 disposed between condition sensor 101 of FIG. 1 and the upper layer of matrix 107. Bonding layer 401 may be the same matrix material as matrix 107, or it may be an adhesive layer such as a pressure-sensitive bonding agent, hot-melt or other adhesive material. In applications where matrix 107 is a poor insulator, layer 401 may be an insulative layer having a resistivity sufficiently high to prevent detrimental response of sensor 101.

FIG. 5 is a cross section of an embodiment of the invention showing condition sensor 101 disposed on composite material 503. Composite material 503 comprises fibers 505 dispersed in resin or matrix 507 as best shown in detail FIG. 5A. In the preferred embodiments, sensor composite matrix 111 (FIG. 1A) is the same polymeric composition as matrix 507.

In an alternative positioning of condition sensor 101, the conductive particles of the condition sensor may be mixed and deposited below the surface of composite material 503 as shown in phantom lines 509. In the preferred embodiments, the matrix of sensor 101 is the same as the matrix of the composite material.

Figure 6:
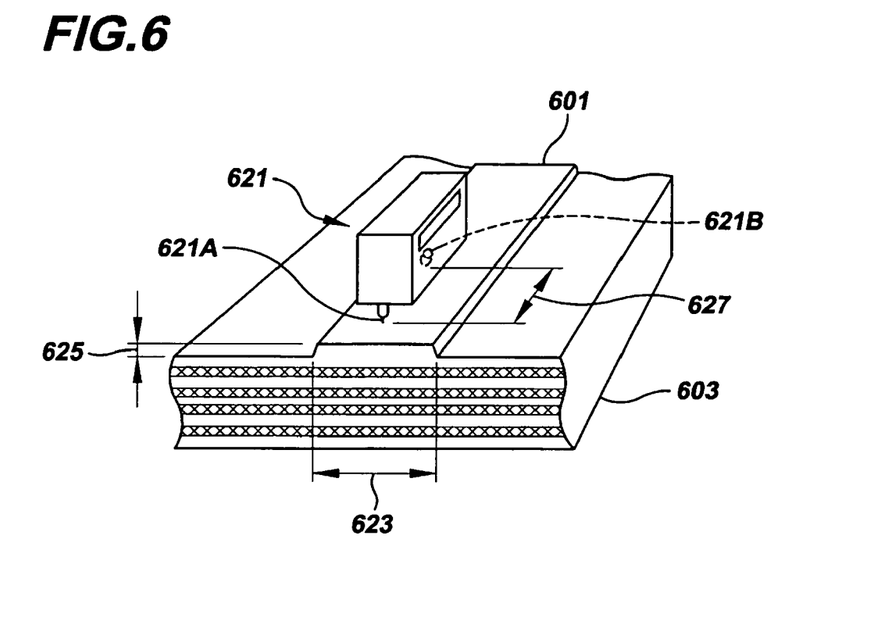
FIG. 6 is a perspective cut-away drawing showing contact of the electrodes of a resistance measuring device to measure the resistance of a condition sensor disposed on the surface of a composite material.

FIG. 6 is a perspective drawing of a resistance measuring instrument 621 being used to measure the resistance of a portion of a condition sensor strip 601 disposed on a composite material 603. Electrodes 621A, 621B allow measurement of resistance of the portion of condition sensor 601 between electrodes 621A, 621B. Instrument 621, such as a high range ohmmeter measures resistance r between electrodes 621A, 621B. The volume resistivity R of portion 601A of sensor strip 601 may be determined by:

$$R=(r)(A/l)=(r)(w)(t)/l$$

Where r=measured resistance of the sensor, w=the width 623 of the sensor 601 strip, t=the thickness 625 of sensor strip 601, and l=the length 627 between electrodes 621A, 621B. The resultant value of R may be used to determine the mechanical properties of the polymer composite as a function of R, for example from data such as that shown in FIG. 3. Lower R threshold limits, based on minimum acceptable mechanical properties may be established for the desired material.

Figure 7:
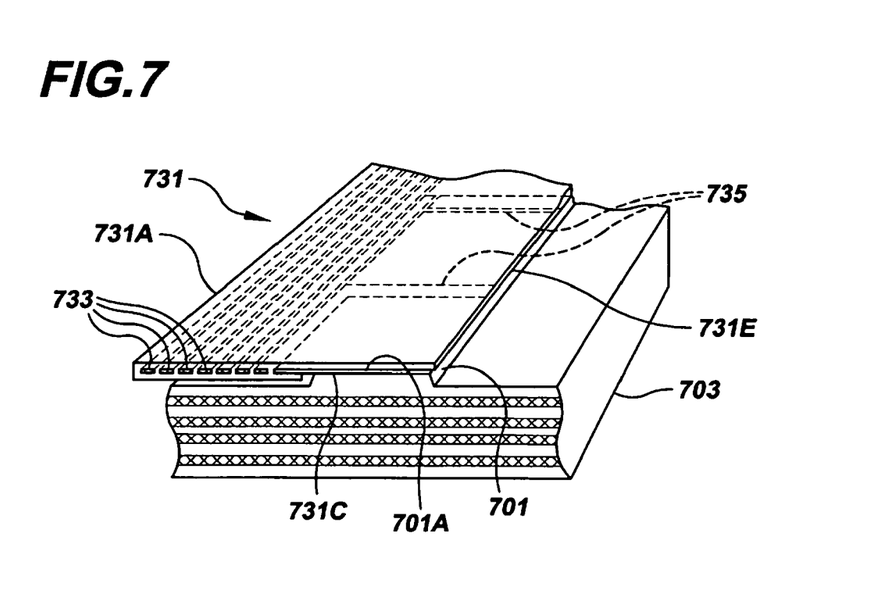
FIG. 7 is a perspective cut-away drawing of a multi-conductor tape with electrodes bonded to the condition sensor of a composite material, the tape used to communicate resistance reading of the condition sensor to a resistance measuring instrument.

FIG. 7 is a perspective drawing of an alternative embodiment of a communications method utilizing a multi-conductor ribbon tape 731 bonded to condition sensor strip 701 of composite material portion 703. Tape 731 may be a polymeric tape such as a polyethyleneterephthalate (PET) tape having ribbon conductors 733 embedded in conductor portion 731A. Electrodes 735, bonded to electrode support portion 731B make mechanical and electrical contact with upper surface 701A of sensor strip 701. Contact surface 731C of tape 731 may be bonded to surface 701A, or alternatively, embedded in sensor surface 701A before curing of sensor strip 701. Conductors 733 may be electrically connected to a connector (not shown) on an end of tape 731, or alternatively connected to other wired or wireless means of communicating resistance measured between electrodes 735. The spacing of electrodes 735, and the width and thickness of sensor strip 701 determine conversion of measured resistance between electrodes and resistivity of the sensor.

Figure 8:
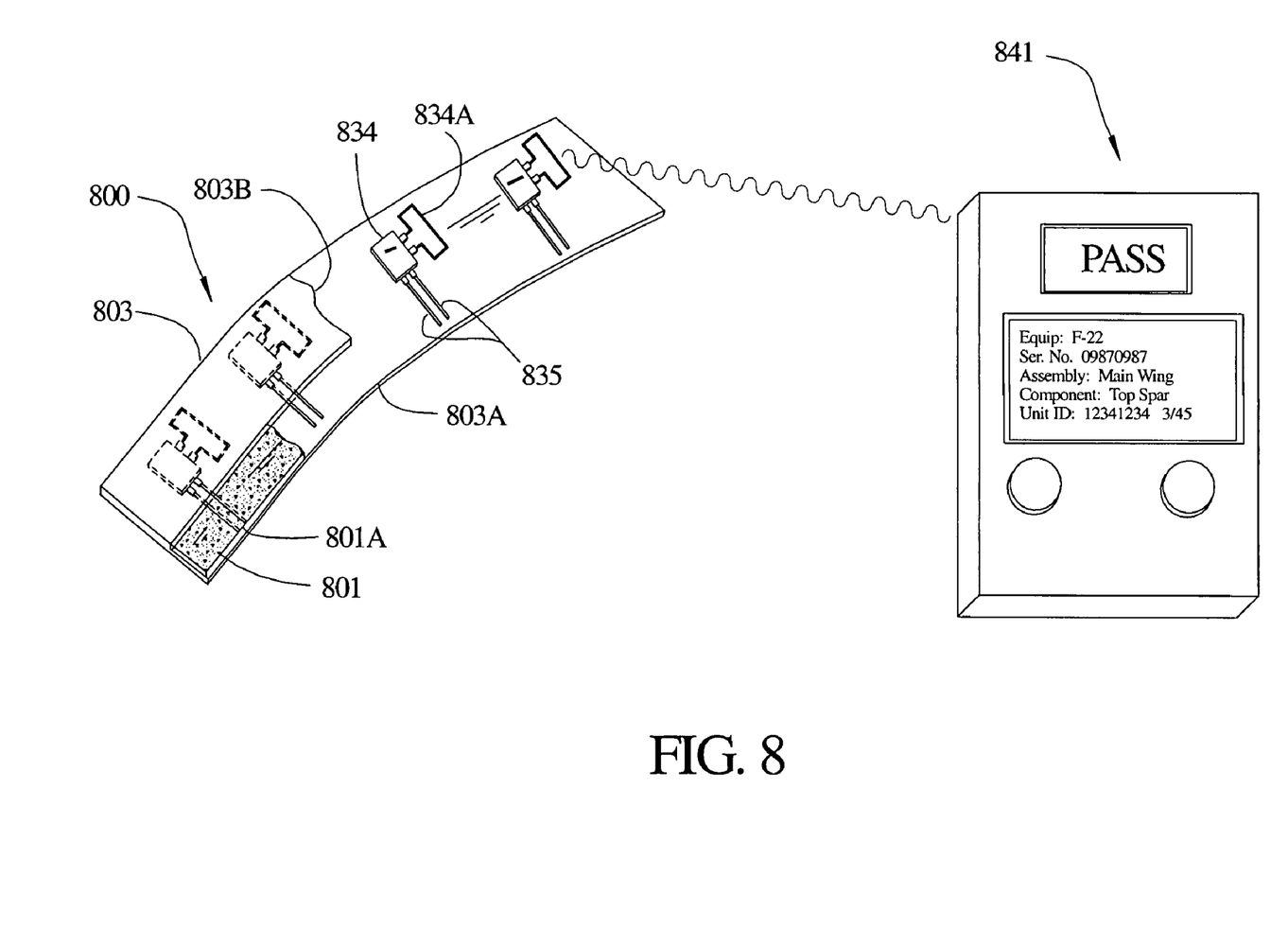
FIG. 8 is a perspective drawing of a communications method utilizing multiple radio frequency identification devices (RFIDs) with electrodes attached to a tape bonded to a sensor strip, and a reader for interrogating and communicating resistivity data from the RFIDs.

FIG. 8 is a perspective drawing of a wireless communications strip 800 communicating resistance measurements of a conductive composite condition sensor 801 to a reader 841. Communications strip 800 comprises a plurality of passive radio frequency identification devices (RFIDs) 834 embedded in a polymeric tape such as a polyester tape 803. Electrodes 835, disposed on tape portion 803A and connected to RFID 834 makes electrical contact with condition sensor 801. Antenna 834A allows communication of sensor portion 801A resistance between sets of electrodes 835 to RFID reader 841. The RFIDs are covered by an auxiliary tape portion 803B. In an alternative embodiment, RFID 834 is embedded in the matrix of the composite.

Figure 9:
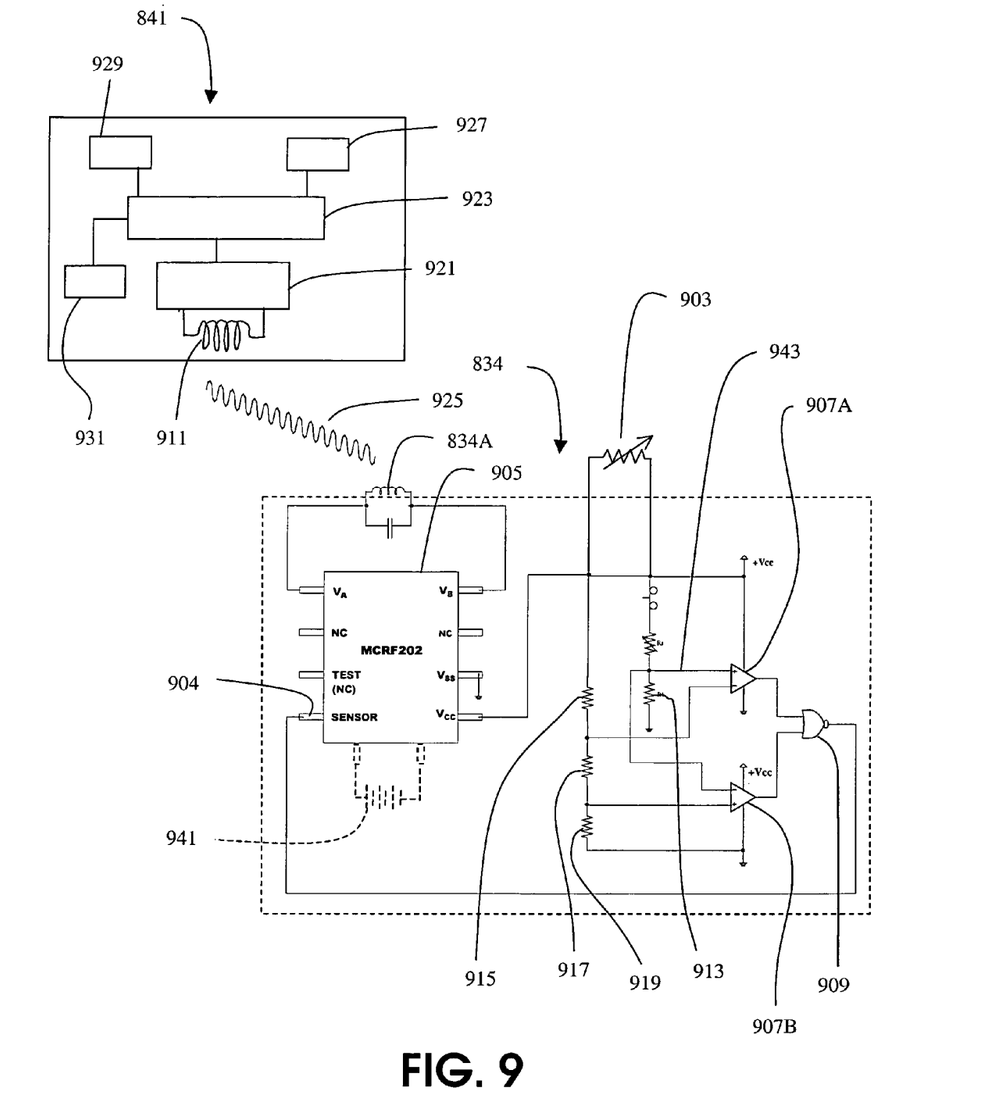
FIG. 9 is a schematic and block diagram of a RFID and reader used to communicate a threshold pass/fail resistivity reading to a RFID reader.

FIG. 9 is a block and schematic diagram of a passive RFID such as RFID 834 of FIG. 8 communicating with a RFID interrogator or reader 841. In the preferred embodiments, RFID 834 is passive (powered by radio frequency energy coupled from reader 841) having an degradation sensor 903 input to provide a "pass/fail" age threshold to reader 841. In the preferred embodiments, RFID chip 905 is a passive RFID chip with an "on-off" sensor input 904 such as a MCRF202 RFID manufactured by Microchip, Inc. RFID chip 905 receives input from threshold comparators 907A, 907B through NOR gate 909 at sensor input 904 and provides the programmed digital identification code upon normal aging condition of sensor 903. Upon a failure mode, RFID chip 905 provides an inverted identification code to reader 841. A failure mode signal is generated by NOR gate 909 if age sensor 903 is aged sufficiently for the resistance of sensor 903 to be less than a threshold value determined by reference resistors 913, 915, 917, 919. A failure mode (inverted code) is also generated if sensor 903 opens. Antenna 834A provides power to the device and communication with reader 841.

In the preferred embodiments, the unique code programmed into the non-volatile memory of RFID chip 905 is associated with application data such as assembly, component and component location in which RFID 834 is installed. Alternatively, related assembly, component manufacturing, and location data may be related by a digital database accessible by reader 841.

Reader 841 utilizes an oscillator/demodulator 921 controlled by a microprocessor 923 to produce the radio frequency energy 925 communicating with, and providing power for, RFID 834. Modulation produced by RFID chip 905 (corresponding with programmed identification code and the state of sensor 903) is demodulated by oscillator/demodulator 921 and microprocessor 923 provides RFID identification and pass/fail criteria to respective indicators 927, 929. Battery 931 provides power for reader 841. Antenna 911 provides communication with antenna 834A of RFID 834. In other embodiments, a separate computer (not shown) may provide the database association and indication functions for reader 841.

In still other embodiments, RFID 905 may be an active RFID with internal volatile memory and a clock. Battery 941, shown in phantom lines provides power for an active RFID. Sensor 903 output at 943 may be connected directly to the sensor input 904. Active RFID 905 would provide the means to periodically store voltage readings corresponding to sensor 903 resistance values. The resistance values would be downloaded upon interrogation by reader 841 and correlated with resistivity values to determine the condition and remaining life of sensor 903.

Figures 10, 10A:
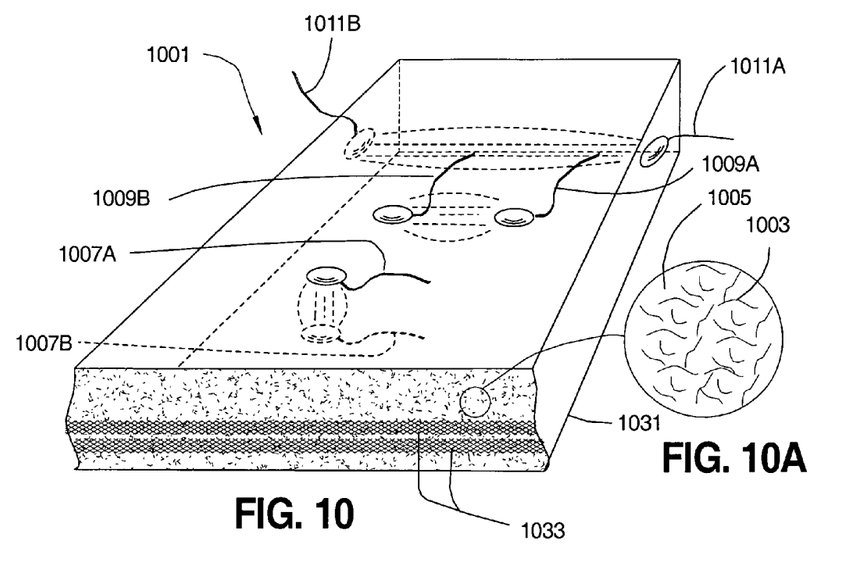
FIG. 10 is a perspective cutaway drawing of an embodiment of the present invention where conductive particles are added to a composite component to create a condition sensor of the component itself by using electrodes to measure the resistance through one or more axis or planes of the component.
FIG. 10A is a detail cross section of the composite component of FIG. 10 showing dispersion of the conductive particles in the matrix of the component.

FIG. 10 is a cutaway perspective drawing showing an alternative embodiment of the present invention showing condition monitoring of a conductive composite component 1001. Component 1001 may be a structural component such as a beam, column, spar, truss or it may be a portion of a body panel, wall panel or other structural components. In still other applications, component 1001 may be a tank, vessel, or piping portion or it may be a decorative component.

In the preferred embodiments, component 1001 is a conductive composite component made of a conductive particle or fiber 1003 dispersed in polymeric matrix 1005, as best shown in FIG. 10A. Polymeric matrix 1005 may be a thermoplastic or thermosetting resin or it may be a commodity or engineered plastic material or blend. Conductive fibers 1003 may be any conductive metal, metal oxide, or semi-metallic particle or fiber. In the preferred embodiments, conductive fiber 1003 is a carbon black particle or fiber and in the most preferred embodiments, fiber 1003 is a carbon nanotube. Highly structured carbon blacks or nanotubes allow the composite to be made conductive with a low volume fraction of the conductive fiber.

In the preferred embodiments, the volume fraction of the conductive fiber is adjusted so that the volume resistivity of the bulk portion of conductive composite component 1001 is in the range 209 of FIG. 2. In the more preferred embodiments, the volume fraction of the conductive fiber is adjusted so that the volume resistivity of the bulk portion of conductive composite component 1001 is between 10E2 and 10E12 ohm-cm. In the most preferred embodiments, the volume fraction of the conductive fiber is adjusted so that the volume resistivity of the bulk portion of conductive composite component 1001 is between 10E4 to 10E10 ohm-cm. Selection of resistivities in these ranges allows reasonable sensitivity to aging mechanisms and reasonable ease of measurement with field instrumentation. Selection of the desired bulk material resistivity may also be made based on considerations such as static dissipative properties, lightening susceptibility, electrical grounding specifications of the component.

Placement of electrode pairs in locations such as those of electrode pairs 1007A, 1007B, 1009A, 1009B, and 1011A, 1011B allows measurement of electrical resistance between the known locations of the electrode pairs. For example, electrode pair 1007A, 1007B measures the resistance of component 1001 in the thickness direction as shown in the figure. In the preferred embodiments, a reference (base case) database is established by making at least one, and preferably a number of resistance measurements at established electrode locations. The electrodes may be portable and placed manually, or they may be moved to predetermined locations by a robotic mechanism (not shown). In still other embodiments, electrode pairs may be bonded or otherwise attached to component 1001 by an adhesive or mechanical fasteners.

The electrodes may be small discrete electrodes as shown, strip or electrodes covering entire surface portions of the component. For example, a surface electrode may be permanently bonded to the back surface 1031 of component 1001, and one or more small electrodes may be placed at predetermined locations on other surfaces of component 1001 to measure degradation. Conductive composite component 1001 may comprise reinforcement fibers in the form of strips, mats or woven sheets 1033.

Figure 11:
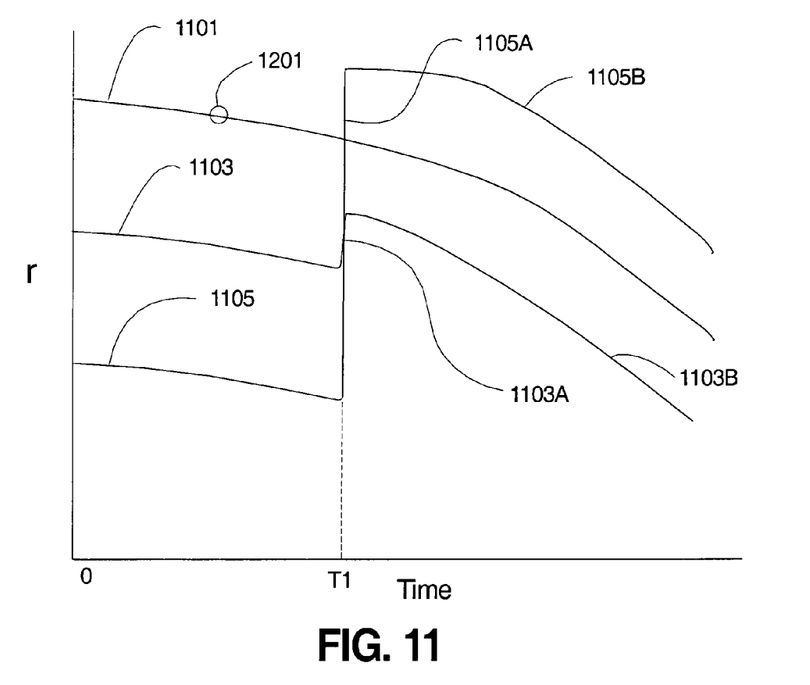
FIG. 11 is a graph showing possible resistance readings for several electrode pairs of the conductive composite component of FIG. 10, showing decrease in resistance of the electrode pairs over time due to chemical and physical aging and increases in resistance due to mechanical flaws.

FIG. 11 is a resistance-time graph showing possible resistance curves 1101, 1103, 1105 of several electrode pairs such as the electrode pairs of FIG. 10. The initial resistance between the pairs of electrodes is represented by the initial resistance at time 0 for each curve. The resistivity of the composite material may be calculated with numerical means or approximated by measurement of a standard specimen in order to correlate mechanical properties or aging effects. The resistance curves measured across baseline locations will decrease with time due to reduction of volume fraction of the conductive particles as discussed previously. Abnormal decreases would be investigated. Significant reduction at some locations with respect to others may indicate abnormally high aging rates, for example due to localized heating. Resistance readings over time should be taken at the same temperature to reduce the effects of resistance changes due to thermal expansion and contraction of the components.

Increases in resistivity such as the increases 1105A, 1103A in curves 1103 and 1105 at time T1 may be indications of mechanical flaws such as cracks. Cracks may appear suddenly, or over time, depending on the composite, stresses, and environment. The effect on resistance readings will depend on the size, location and orientation of the crack. For example, large cracks in a plane perpendicular and directly between electrodes will result in a large increase in resistivity. Other electrode pairs where the crack is small or more distant to the electrodes, or the plane is not perpendicular to the field lines of the electrode pair will result in smaller changes. Should the mechanical flaw remain stable the resistance curves will continue to decrease as shown in 1105B, 1103B. Increases in crack size with time will result in further increases in resistance of the affected electrode pairs. Investigation of the electrode location and magnitude of change will provide a means for further investigation, such as by radiography or ultrasonic examination techniques known in the art.

Figure 12:
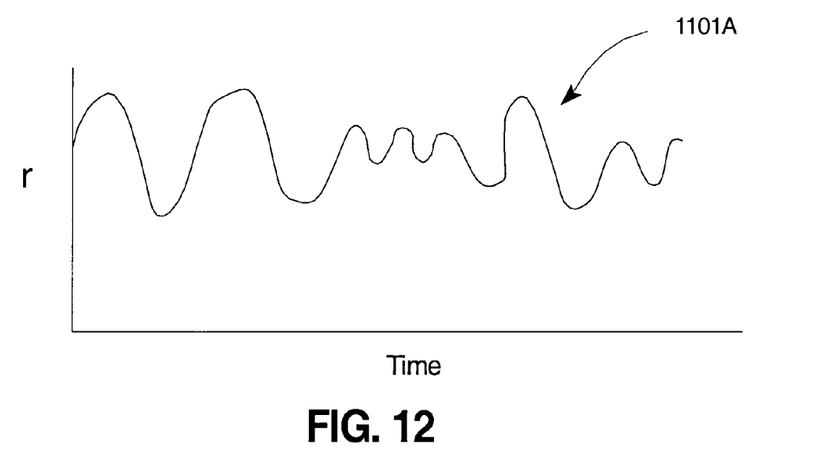
FIG. 12 is a resistance-time graph of a short time period of a condition sensor over a short time interval showing the response to short-time stress/strain effects in the component.

FIG. 12 is a resistance-time plot for curve 1101A taken over a very short time interval 1201 of FIG. 11. The short time scale variations of resistance of electrode pairs such as the electrode pairs of FIG. 10 provide a resistance response to stress-strain conditions of composite component 1001. For example, a cyclic stress on component 1001 produces a corresponding cyclic strain and results in a cyclic resistance response of an electrode pair positioned on component 1001. Comparison of the resistance values of the electrode pairs using known stresses on component 1001 provides a means to correlate sensor output with applied stresses on the component. Analytical and modeling approaches may also be used to correlate sensor output with stress-strain conditions of the component.

Accordingly, the reader will see that Health Monitoring Method and Sensor Apparatus for Composite Materials provides an in-situ, non-destructive method for indirect measurement of mechanical properties and indication of remaining age of composite materials. The method and materials of the presents invention provides the following additional advantages:

The method may be used on virtually any polymeric material when combined with a conductive filler material;
Simple, low-cost instrumentation may be used;
The method is compatible with other NDT methods; and
The method is simple, requires minimal operator training, and is low in cost.

Although the description above contains many specifications, these should not be construed as limiting the scope of the invention but merely providing illustrations of some of the presently preferred embodiments of this invention. For example, the age sensor of this invention may be applied to other materials and products besides composite materials. The resistivity of this "universal" sensor may be correlated to the condition of the material or product by natural or acceleration aging of the material or product and comparing with the resistivity of the sensor. Numerical techniques such as Arrhenius methodology or empirical comparisons may be made to correlate sensor resistivity with mechanical properties and remaining age of the material or product monitored.

Thus the scope of the invention should be determined by the appended claims and their legal equivalents, rather than by the examples given.

We claim:

1. A method for monitoring the health of a composite structure comprising a polymeric structural matrix, the method comprising the steps of:
   disposing a condition sensor mechanically coupled with said polymeric structural matrix of said composite structure, said condition sensor comprising a polymeric sensor matrix and a selected quantity of conductive particles;
   measuring resistivity of said condition sensor with a pair of electrodes in a predetermined location wherein the predetermined location is defined by the location of said condition sensor;
   comparing said resistivity measurement with resistivity of an aged condition sensor; and
   equating said resistivity of said condition sensor to said health of said composite structure by associating a decrease in resistivity of said condition sensor over time to chemical aging of said composite structure and an increase in resistivity over time to a mechanical flaw of said composite structure between said predetermined location of said pair of electrodes.

2. The method for monitoring the health of a composite structure of claim 1 wherein said polymeric structural matrix comprises a first polymer and said sensor matrix comprises said first polymer.

3. The method for monitoring the health of a composite structure of claim 1 wherein said conductive particles comprise carbon.

4. The method for monitoring the health of a composite structure of claim 3 wherein said conductive particles comprise carbon black particles.

5. The method for monitoring the health of a composite structure of claim 3 wherein said conductive particles form carbon nanotubes.

6. The method for monitoring the health of a composite structure of claim 1 wherein said conductive particles comprise metallic particles.

7. The method for monitoring the health of a composite structure of claim 1 wherein said condition sensor is bonded to a first portion of said polymeric structural matrix.

8. The method for monitoring the health of a composite structure of claim 7 wherein said first portion of said composite structural matrix is disposed between a web of a reinforcement fiber and a surface of said composite structure.

9. The method for monitoring the health of a composite structure of claim 8 wherein said condition sensor is bonded to said first portion of said composite structural matrix by said polymeric sensor matrix.

10. The method for monitoring the health of a composite structure of claim 9 wherein said selected quantity of conductive particles provides a resistivity of said condition sensor less than a resistivity of said polymeric structural matrix.

11. The method for monitoring the health of a composite structure of claim 1 comprising an electrical insulative material disposed between said condition sensor and said polymeric structural matrix.

12. The method for monitoring the health of a composite structure of claim 1 wherein said condition sensor comprises an attached electrode for measuring said resistance of said condition sensor.

13. The method for monitoring the health of a composite structure of claim 12 wherein a plurality of electrodes are disposed on a membrane bonded to said condition sensor.

14. The method for monitoring the health of a composite structure of claim 1 wherein said condition sensor is disposed on an outside surface portion of said composite structure and said resistivity is measured by electrode contact with an outside surface portion of said condition sensor.

15. The method for monitoring the health of a composite structure of claim 1 wherein time domain analysis is used to distinguish chemical aging and mechanical flaw damage of said composite structure.

16. A method for monitoring the health of a composite structure comprising a polymeric structural matrix, the method comprising the steps of:

disposing a condition sensor in said polymeric structural matrix of said composite structure, said condition sensor comprising a selected quantity of conductive particles disposed in said polymeric structural matrix;

measuring a resistivity of said condition sensor with a pair of electrodes in a predetermined location;

comparing said resistivity measurement with resistivity of an aged condition sensor; and equating said resistivity of said condition sensor to said health of said composite structure by associating a decrease in resistivity of said condition sensor over time to chemical aging of said composite structure and an increase in resistivity over time to a mechanical flaw of said composite structure between said predetermined location of said pair of electrodes.

* * * * *